(12) United States Patent
Akui

(10) Patent No.: US 10,231,605 B2
(45) Date of Patent: Mar. 19, 2019

(54) ENDOSCOPE

(71) Applicant: OLYMPUS CORPORATION, Tokyo (JP)

(72) Inventor: Nobuaki Akui, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 98 days.

(21) Appl. No.: 15/201,703

(22) Filed: Jul. 5, 2016

(65) Prior Publication Data

US 2016/0309985 A1    Oct. 27, 2016

Related U.S. Application Data

(63) Continuation of application No. PCT/JP2015/058328, filed on Mar. 19, 2015.

(30) Foreign Application Priority Data

May 16, 2014    (JP) .................................. 2014-102625

(51) Int. Cl.
*A61B 1/00*    (2006.01)
*A61B 1/005*    (2006.01)
(Continued)

(52) U.S. Cl.
CPC .......... *A61B 1/0057* (2013.01); *A61B 1/0052* (2013.01); *A61B 1/04* (2013.01);
(Continued)

(58) Field of Classification Search
CPC ............................ A61B 1/0052; A61B 1/0057
(Continued)

(56) References Cited

U.S. PATENT DOCUMENTS 5,609,563 A * 3/1997 Suzuki .............. A61B 1/00098
600/107
5,846,183 A * 12/1998 Chilcoat ............ A61B 1/00142
600/112

(Continued)

FOREIGN PATENT DOCUMENTS

EP    2505117 A1    10/2012
EP    2649921 A1    10/2013
(Continued)

OTHER PUBLICATIONS

International Search Report dated Jun. 16, 2015 issued in PCT/JP2015/058328.

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

There is provided an endoscope capable of realizing equal operability by either a left or right hand without upsizing an operation portion. For this purpose, an operation portion is formed in a bilaterally symmetrical shape; a suction button and a bending lever are disposed at a center in a left and right width direction of the operation portion facing each other; and respective arm portions are disposed in a state of being rotated around a central axis of the bending lever by a predetermined angle relative to up, down, left and right tilt directions defined for the bending lever.

6 Claims, 10 Drawing Sheets

(51) Int. Cl.
*A61B 1/04* (2006.01)
*A61M 25/01* (2006.01)
*A61B 1/015* (2006.01)

(52) U.S. Cl.
CPC .... *A61M 25/0138* (2013.01); *A61M 25/0147* (2013.01); *A61B 1/015* (2013.01)

(58) Field of Classification Search
USPC ........................................ 600/146, 152, 149
See application file for complete search history.

(56) References Cited

U.S. PATENT DOCUMENTS

| | | | | |
|---|---|---|---|---|
| 5,924,978 | A * | 7/1999 | Koeda | .................. G02B 6/0006 600/131 |
| 6,991,603 | B2 * | 1/2006 | Krupa | ................ A61B 1/00071 138/119 |
| 7,722,532 | B2 * | 5/2010 | Ikeda | .................. A61B 1/00039 600/102 |
| 2009/0209822 | A1 * | 8/2009 | Ikeda | .................. A61B 1/00091 600/157 |
| 2012/0071864 | A1 | 3/2012 | Banju et al. | |
| 2013/0047755 | A1 * | 2/2013 | Okamoto | ............. A61B 1/0052 74/89.2 |

FOREIGN PATENT DOCUMENTS

| | | | |
|---|---|---|---|
| JP | 62-281918 | * | 12/1987 |
| JP | 08313827 A | * | 11/1996 |
| JP | H08-299255 A | | 11/1996 |
| JP | 2003-325437 A | | 11/2003 |
| JP | 5011454 B | | 8/2012 |
| JP | 5309265 B2 | | 10/2013 |
| WO | WO 2011/111258 A1 | | 9/2011 |
| WO | WO 2012/117836 A1 | | 9/2012 |

* cited by examiner

ENDOSCOPE

CROSS REFERENCE TO RELATED APPLICATION

This application is a continuation application of PCT/JP2015/058328 filed on Mar. 19, 2015 and claims benefit of Japanese Application No. 2014-102625 filed in Japan on May 16, 2014, the entire contents of which are incorporated herein by this reference.

BACKGROUND OF INVENTION

1. Field of the Invention

The present invention relates to an endoscope in which a bending portion performs a bending motion in conjunction with an operation of tilting a bending lever.

2. Description of the Related Art

Conventionally, endoscopes have been widely used in medical and industrial fields. Some endoscopes are provided with an elongated and flexible insertion portion. In general, such flexible endoscopes are provided with a bending portion capable of freely performing a bending motion in a predetermined direction in accordance with a user's manual operation, on a distal end side of the insertion portion.

Among the endoscopes, especially in a small-diameter endoscope for which an amount of force for bending is small, and the bending portion of which bends with a small radius of curvature, such as a bronchial endoscope, each portion is generally configured so that a grasping portion provided on the operation portion is grasped by three fingers of a middle finger, a third finger and a little finger of a left hand, a bending lever is operated by a thumb, and various kinds of switches/buttons such as a suction button are operated by a forefinger. Further, in order to easily realize a similar operation not only by a left hand but also by a right hand on an endoscope of this kind, for example, Japanese Patent Application Laid-Open Publication No. H8-299255 discloses a technique in which the bending lever is extended backward from a side portion of the operation portion in an L shape, a finger hooking portion is disposed on a back side of the operation portion, and a suction button is disposed on a longitudinal-direction central axis of the operation portion, on a switch portion set on a front side of the operation portion.

By the way, as for the endoscope with a small diameter, such as a bronchial endoscope, it is also demanded to cause the bending portion to perform a bending motion not only in two directions, such as up and down directions, but also in any of directions including up, down, left and right directions. As a technique for realizing such a bending motion by an operation input to a single bending lever, for example, Japanese Patent Application Laid-Open Publication No. 2003-325437 discloses a bending apparatus provided with a wire pulling member having four arm portions to which proximal end portions of pulling wires (pulling members) corresponding to up, down, left and right bending directions are fixed, respectively, and an operation instruction lever (bending lever) for giving an instruction to cause a tilt direction of and an amount of tilt of the wire pulling member to change and cause a predetermined pulling wire, among the respective pulling wires, to move by a predetermined amount.

SUMMARY OF THE INVENTION

An endoscope according to an aspect of the present invention includes: an insertion portion insertable into a subject and having a bending portion bendable in all directions including four directions of up, down, left and right directions with a longitudinal axis as a center; four wires configured to cause the bending portion to bend by pulling, distal end sides of the four wires being inserted through the insertion portion; an operation portion linked to a proximal end of the insertion portion; an operation button projectingly disposed at a center in a left and right width direction of the operation portion; a button linking member provided in the operation portion and linked to the operation button; an operation lever disposed at the center in the left and right width direction of the operation portion so that the operation lever and the operation button face each other in front and behind, and tiltable in all directions including four directions corresponding to the up, down, left and right directions of the bending portion; and a wire pulling member tiltably provided in the operation portion, the operation lever being coupled with a central part of the wire pulling member, and proximal end sides of the wires being coupled with respective distal end sides of four arm portions extended in cross directions from the central part; wherein tilt directions of the operation lever for causing the bending portion to bend in the up, down, left and right directions are set to correspond to four directions of the left and right width directions of the operation portion and directions orthogonal to the left and right width directions, respectively; extending directions of the four arm portions of the wire pulling member are disposed at positions rotated around a central axis of the operation lever by a set angle relative to the four tilt directions set for the operation lever; and the button linking member is provided at a position facing the wire pulling member and is positioned between and faced by two arm portions among the four arm portions so that the four arm portions do not interfere with the button linking member.

DETAILED DESCRIPTION OF THE PREFERRED EMBODIMENT(S)

Figure 1:
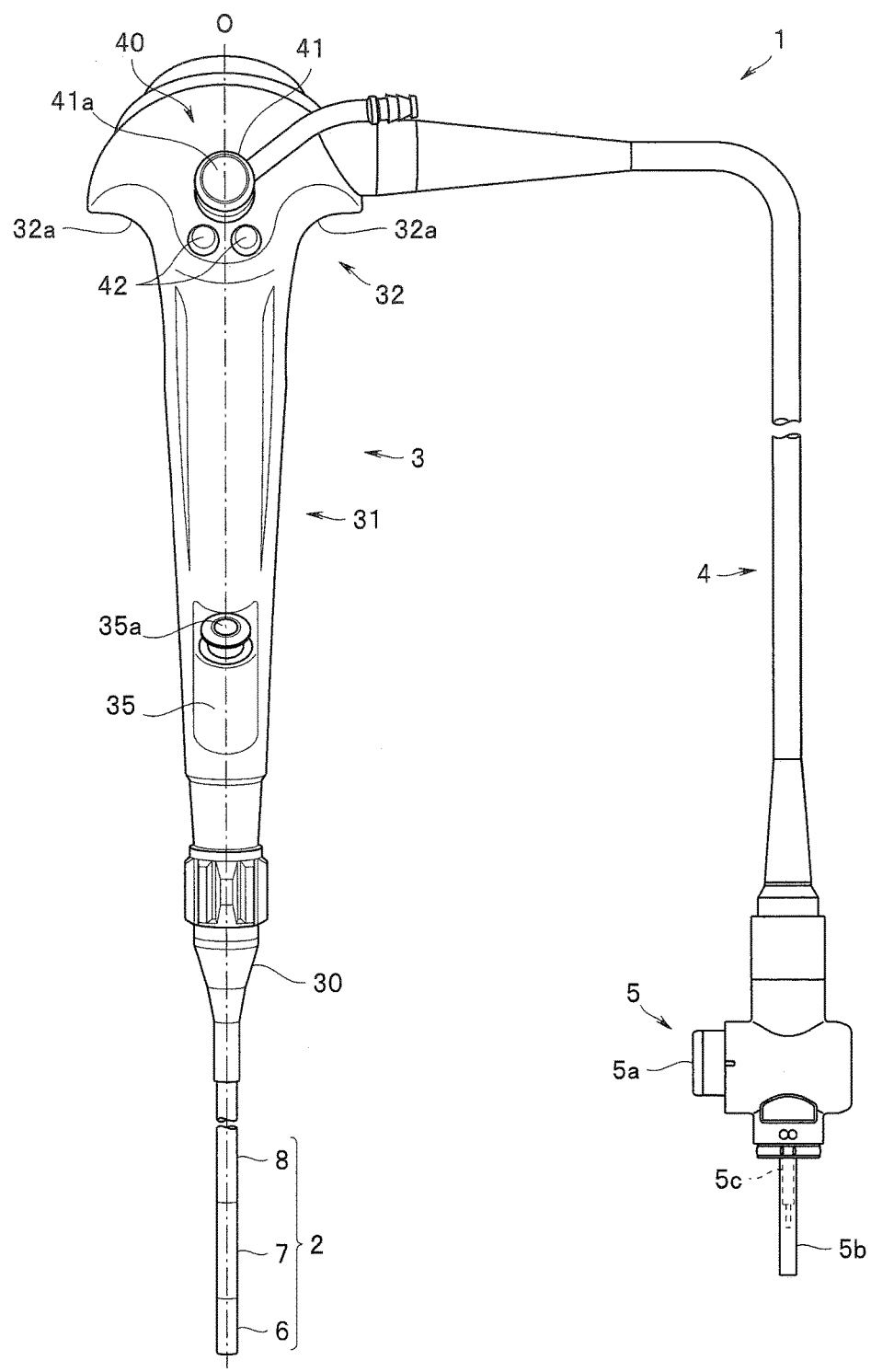
FIG. 1 is a front view showing an external appearance of an endoscope.
Figure 2:
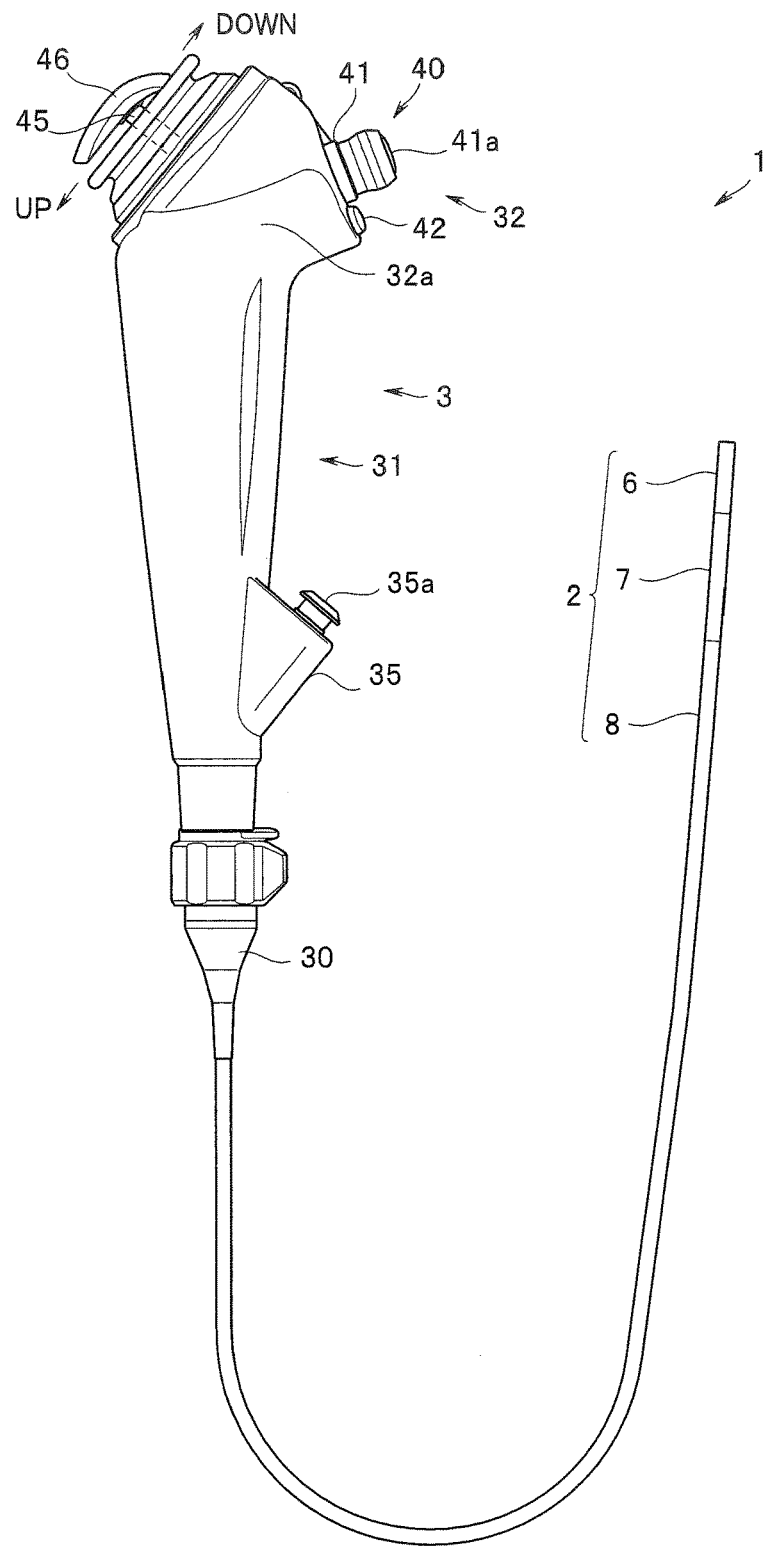
FIG. 2 is a right side view showing the external appearance of the endoscope.
Figure 3:
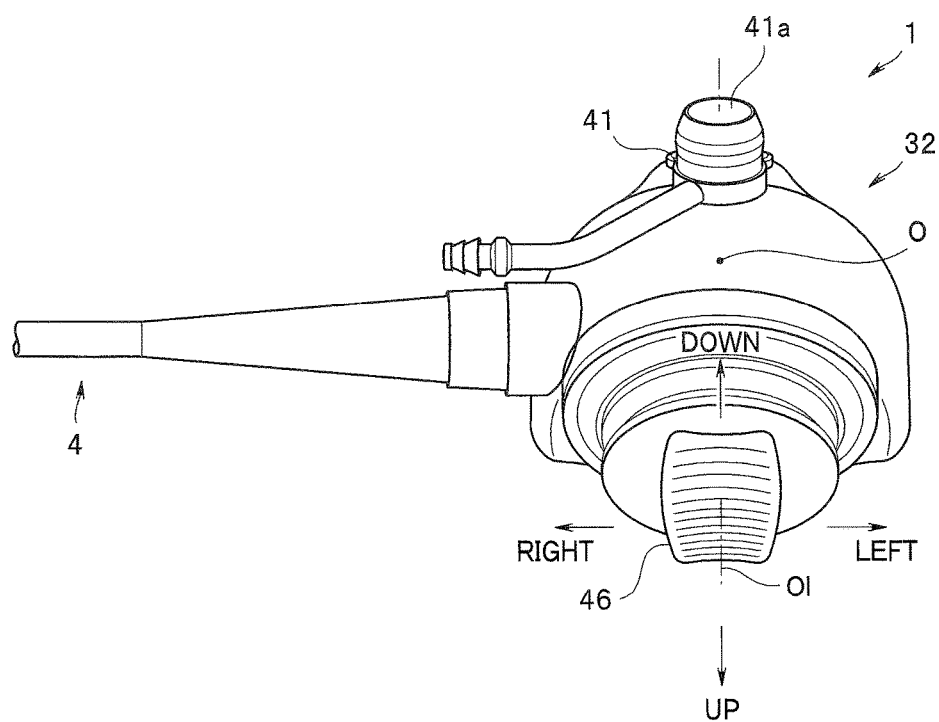
FIG. 3 is a top view showing the external appearance of the endoscope.
Figure 4:
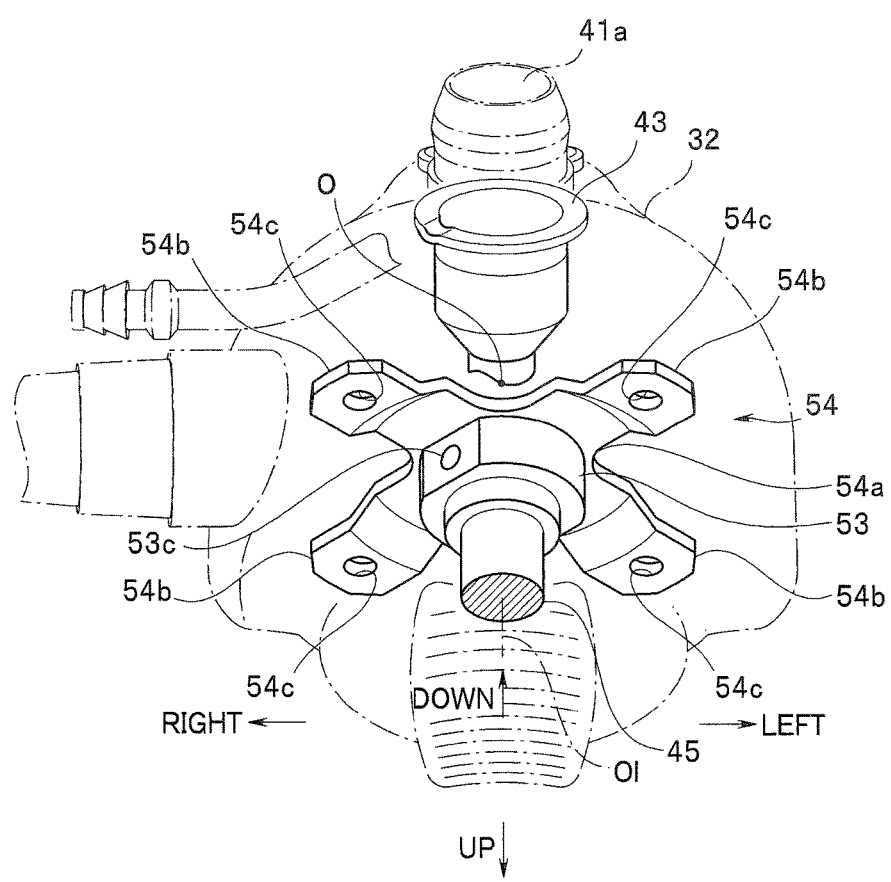
FIG. 4 is an explanatory diagram showing an arrangement relationship between a wire pulling member and a cylinder.
Figure 5:
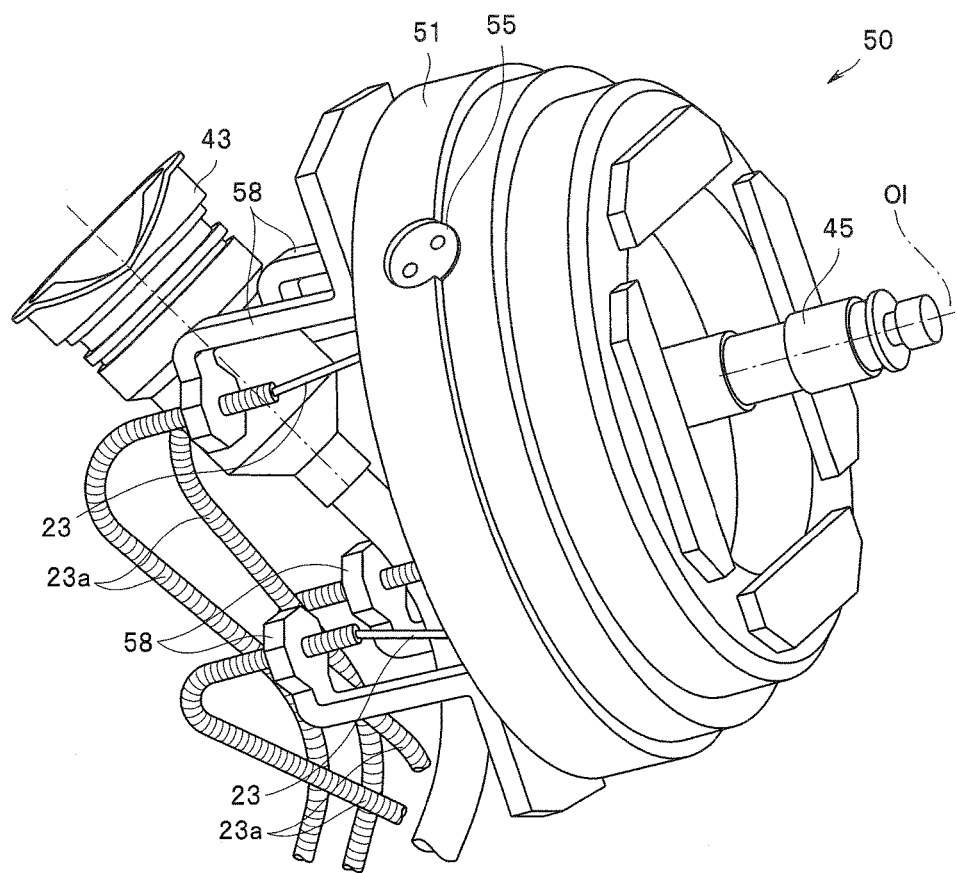
FIG. 5 is a perspective view showing an arrangement relationship between a bending operation mechanism and the cylinder.
Figure 6:
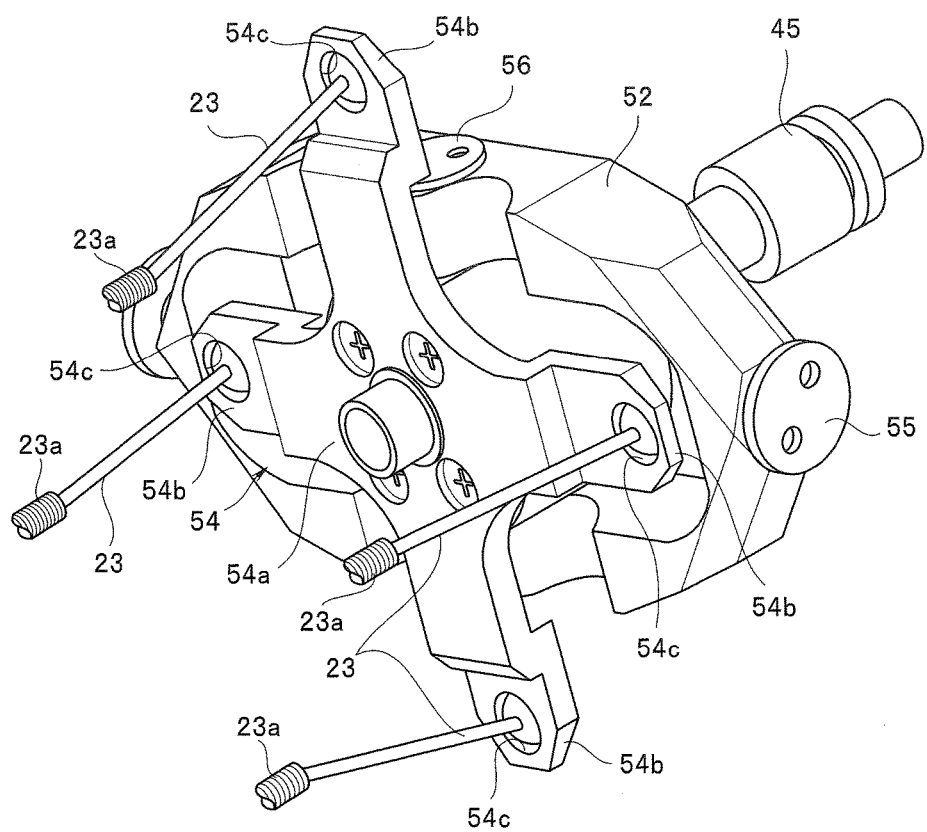
FIG. 6 is a perspective view showing an internal structure body of the bending operation mechanism.
Figure 7:
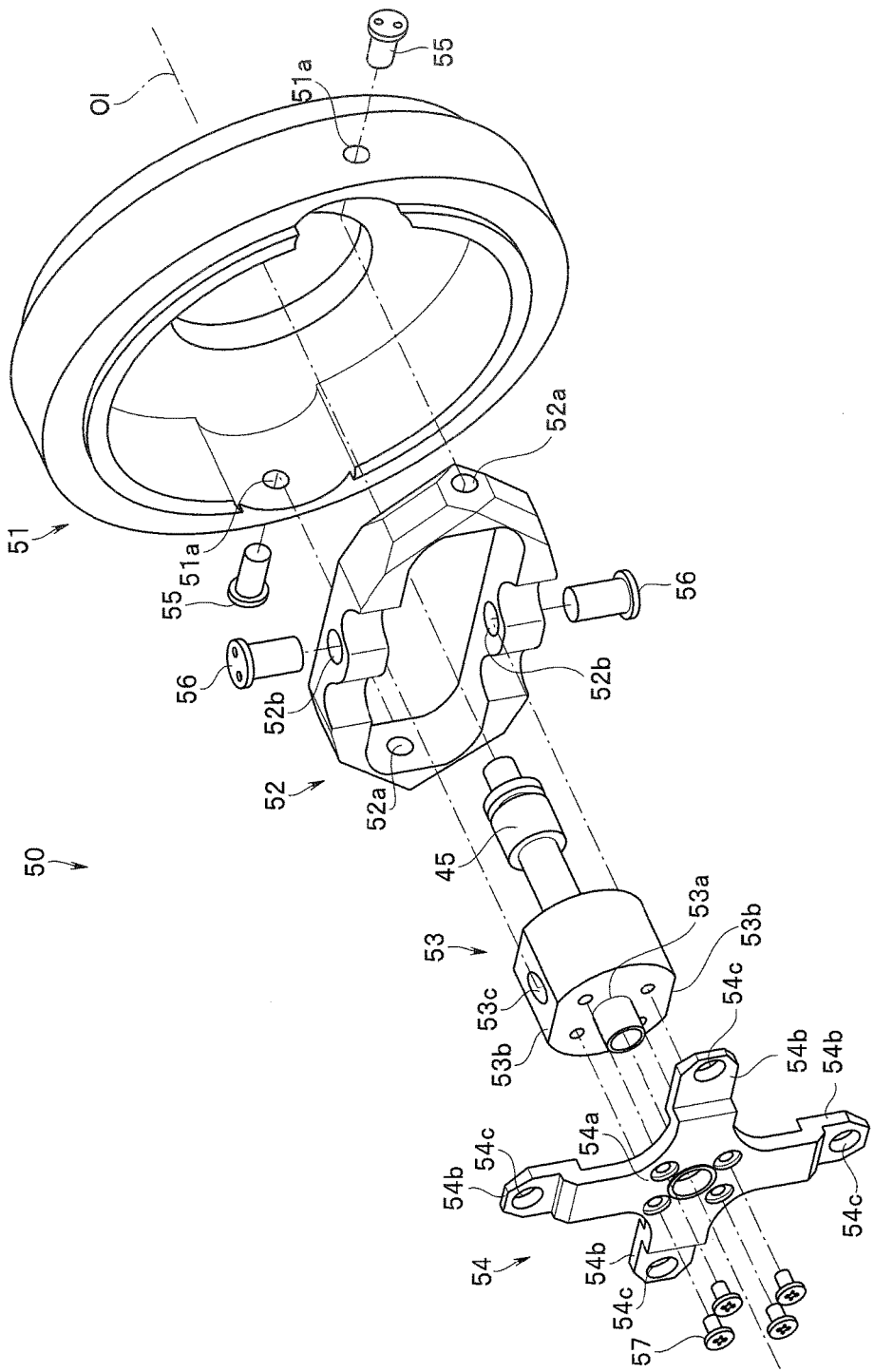
FIG. 7 is an exploded perspective view showing the internal structure body of the bending operation mechanism.
Figure 8:
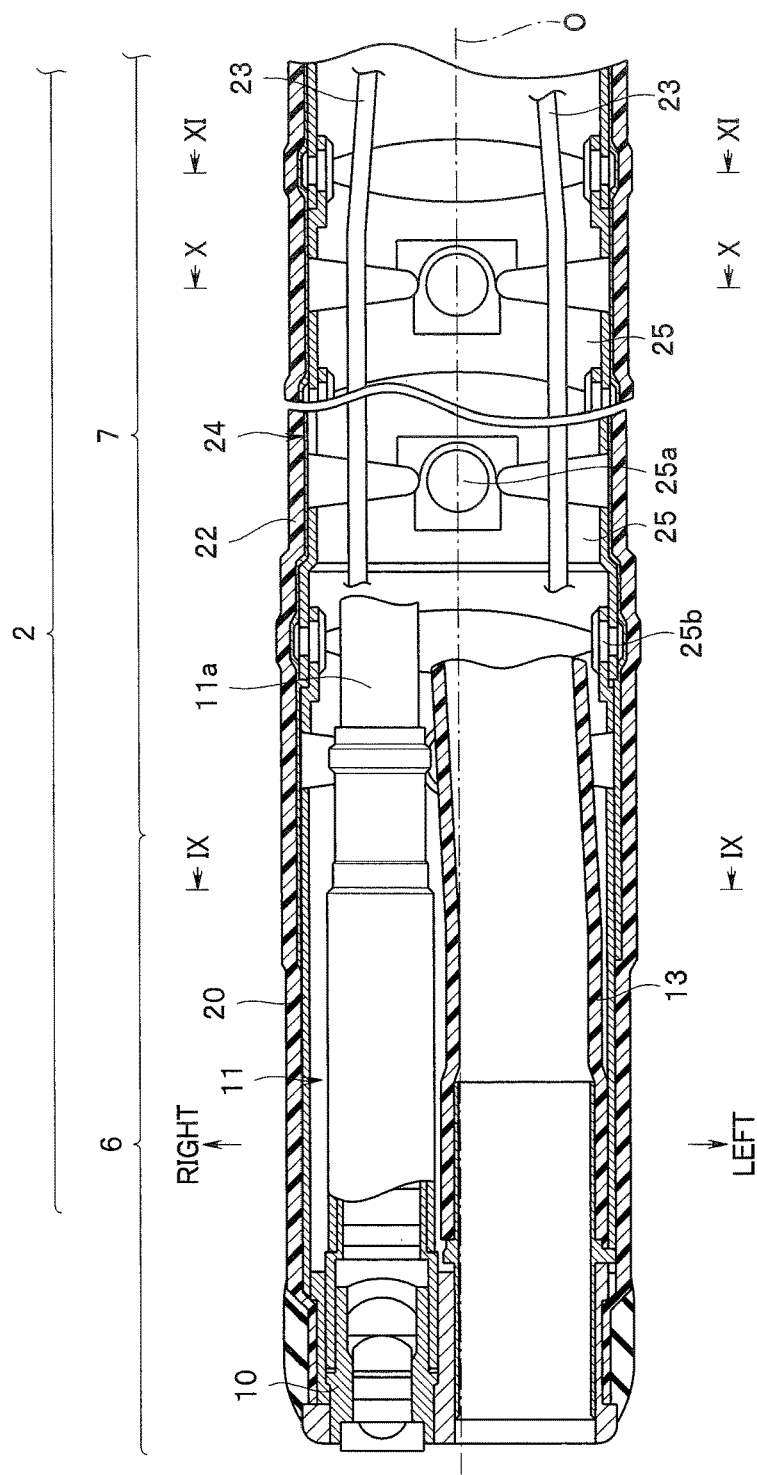
FIG. 8 is a cross-sectional view showing main portions of a distal end portion and a bending portion.
Figure 9:
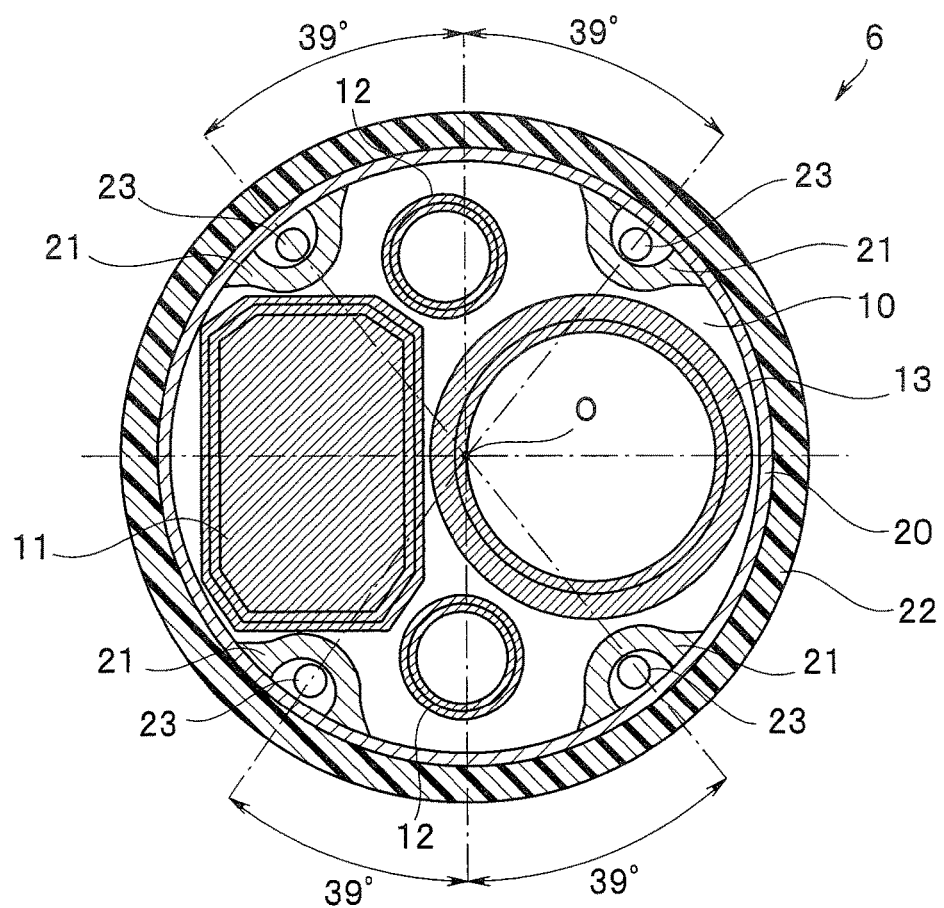
FIG. 9 is a sectional view showing the distal end portion along a IX-IX line in FIG. 8.
Figure 10:
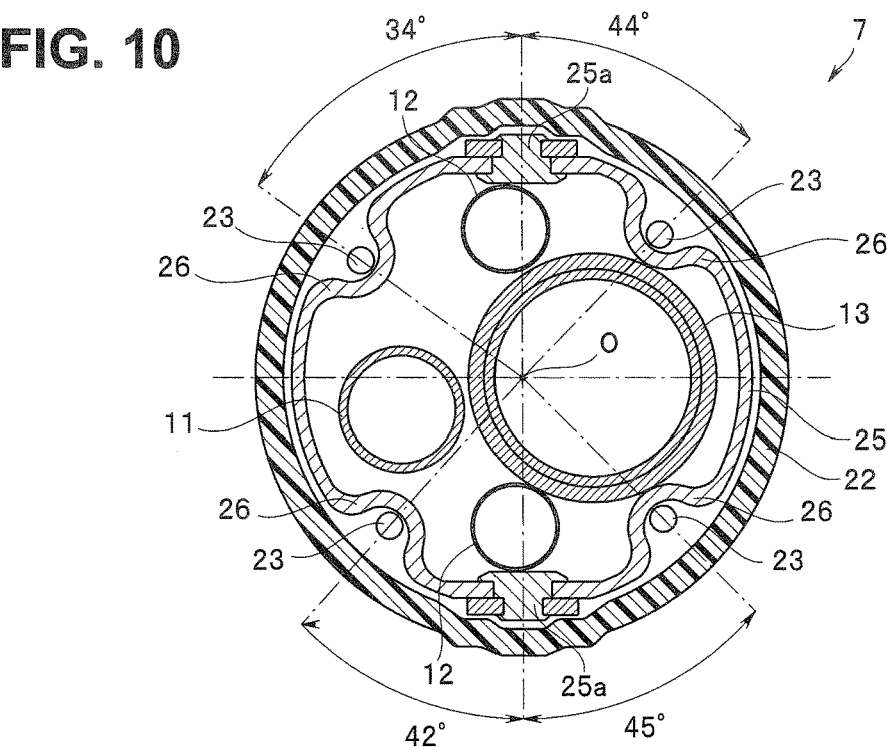
FIG. 10 is a sectional view showing the bending portion along a X-X line in FIG. 8.
Figure 11:
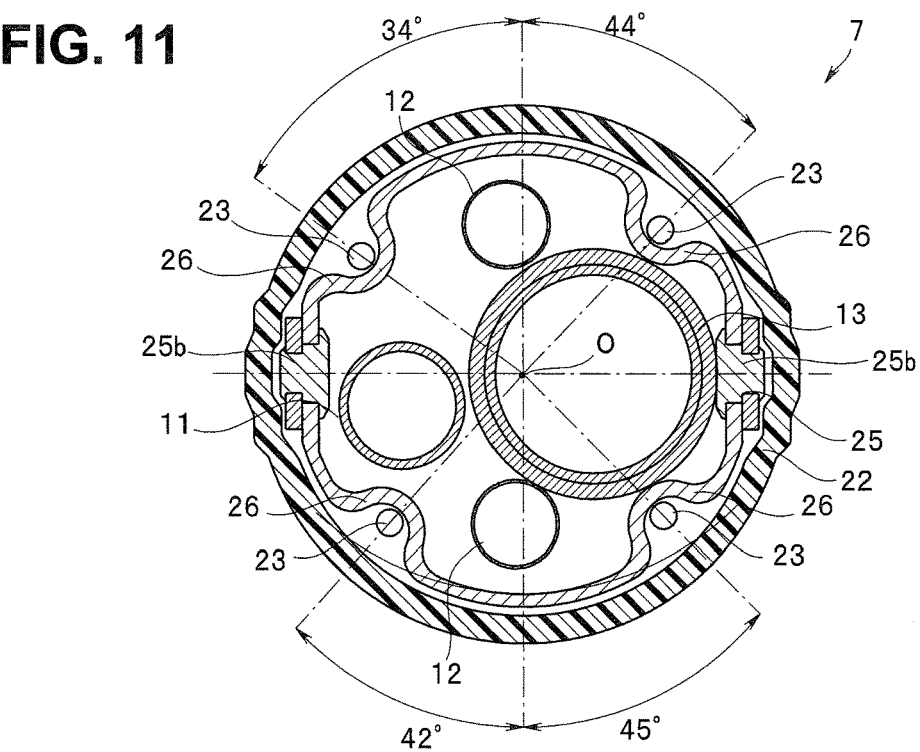
FIG. 11 is a sectional view showing the bending portion along an XI-XI line in FIG. 8.

An embodiment of the present invention will be described with reference to drawings. The drawings are related to the embodiment of the present invention. FIG. 1 is a front view showing an external appearance of an endoscope; FIG. 2 is a right side view showing the external appearance of the endoscope; FIG. 3 is a top view showing the external appearance of the endoscope; FIG. 4 is an explanatory diagram showing an arrangement relationship between a wire pulling member and a cylinder; FIG. 5 is a perspective view showing an arrangement relationship between a bending operation mechanism and the cylinder; FIG. 6 is a perspective view showing an internal structure body of the bending operation mechanism; FIG. 7 is an exploded perspective view showing the internal structure body of the bending operation mechanism; FIG. 8 is a cross-sectional view showing main portions of a distal end portion and a bending portion; FIG. 9 is a sectional view showing the distal end portion along a IX-IX line in FIG. 8; FIG. 10 is a sectional view showing the bending portion along a X-X line in FIG. 8; and FIG. 11 is a sectional view showing the bending portion along an XI-XI line in FIG. 8.

An endoscope 1 of the present embodiment shown in FIGS. 1 and 2 is a bronchial electronic endoscope, and the endoscope 1 is configured having an insertion portion 2 formed in an elongated tube shape, an operation portion 3 linked to a proximal end of the insertion portion 2, a universal cord 4, which is an endoscope cable disposed extending from the operation portion 3, and an endoscope connector 5 disposed at a distal end of the universal cord 4.

The insertion portion 2 is configured with a tubular member having flexibility to which a distal end portion 6, a bending portion 7 and a flexible tube portion 8 are linked in this order from the distal end side.

For example, as shown in FIGS. 8 and 9, a distal end rigid portion 10 made of metal is provided in the distal end portion 6, and, in the distal end rigid portion 10, an image pickup unit 11 which includes an image pickup device such as a CCD and a CMOS, a pair of light guides 12 and a treatment instrument insertion channel 13 are held.

Further, in the distal end portion 6, a most distal end bending piece 20 forming a substantially cylindrical shape is fitted on a proximal end side of the distal end rigid portion 10, and an outer circumference of the most distal end bending piece 20 is covered with bending rubber 22. On an inner circumference of the most distal end bending piece 20, wire fixing portions 21 are provided at four positions around an insertion axis O. A distal end of any one of four pulling wires 23 inserted through the insertion portion 2 is fixed to each of the wire fixing portions 21.

Here, in order to efficiently dispose each component member without increasing a diameter of the distal end portion 6, the image pickup unit 11, which is a large-sized member, and the treatment instrument insertion channel 13 are arranged side by side on right and left in the distal end rigid portion 10 and the most distal end bending piece 20 (see FIGS. 8 and 9), and the respective light guides 12 are disposed in spaces formed above and below by the arrangement. Note that, in the present embodiment, up, down, left and right directions of the distal end portion 6 (insertion portion 2) are, for example, directions defined to correspond to up, down, left and right directions of an image picked up by the image pickup unit 11.

Further, in order to prevent interference of the image pickup unit 11 and the treatment instrument insertion channel 13 with each pulling wire 23, the respective wire fixing portions 21 are provided at positions rotated around the insertion axis O by a predetermined angle relative to the up, down, left and right positions of the distal end portion 6. That is, for example, as shown in FIG. 9, the most distal end bending piece 20 is provided with the respective wire fixing portions 21 at positions rotated left and right, respectively, around the insertion axis O by an angle within a range of 30 to 60 degrees (more specifically, for example, positions rotated left and right by 39 degrees, respectively), with the up direction of the distal end portion 6 as a reference, and positions rotated left and right, respectively, around the insertion axis O by an angle within the range of 30 to 60 degrees (more specifically, for example, positions rotated left and right by 39 degrees, respectively), with the down direction of the distal end portion 6 as a reference. In other words, the respective pulling wires 23 are routed at positions rotated around the insertion axis O by a predetermined angle relative to the up, down, left and right directions, respectively, in the distal end portion 6.

The bending portion 7 is configured so that the bending portion 7 can be caused to actively bend in all circumferential directions around the insertion axis O, including the up, down, left and right directions, in response to an operation input to the operation portion 3 by a surgeon or the like. That is, the bending portion 7 of the present embodiment is configured having a bending piece set 24, for example, in which a plurality of bending pieces 25 are linked and which has pivoted portions 25a disposed in the up and down directions of the insertion portion 2 (see FIG. 8) on a distal end side, and pivoted portions 25b disposed in the left and right directions of the insertion portion 2 on a proximal end side.

Inside the bending piece set 24, a signal cable 11a which extend from the image pickup unit 11, the light guides 12 and the treatment instrument insertion channel 13 are inserted in an arrangement substantially similar to an arrangement in the distal end portion 6. Further, an outer circumference of the bending piece set 24 is covered with the bending rubber 22 extending from a distal end portion 6 side.

Further, on a predetermined bending piece 25 constituting the bending piece set 24, wire guides 26 in which the respective pulling wires 23 are to be inserted are formed. Similarly to the wire fixing portions 21 described above, the wire guides 26 are provided at positions rotated around the insertion axis O by a predetermined angle relative to up, down, left and right positions of the bending portion 7. That is, for example, as shown in FIGS. 10 and 11, the predetermined bending piece 25 is provided with the respective wire guides 26 at positions rotated left and right, respectively, around the insertion axis O by an angle within a range of 30 to 60 degrees (more specifically, for example, positions rotated to a left side by 34 degrees and to a right side by 44 degrees, respectively) with the up direction of the bending portion 7 as a reference, and positions rotated left and right, respectively, around the insertion axis O by an angle within the range of 30 to 60 degrees (more specifically, for example, positions rotated to the left side by 42 degrees and to the right side by 45 degrees, respectively) with the down direction of the bending portion 7 as a reference. In other words, the respective pulling wires 23 are routed at positions rotated around the insertion axis O relative to the up, down, left and right directions, respectively, in the bending portion 7.

The flexible tube portion 8 is configured with a tubular member having flexibility of being passively bendable. Inside the flexible tube portion 8, the signal cable 11a, light guides 12 and treatment instrument insertion channel 13 described above are inserted (none of them is shown here).

The operation portion 3 is configured having a bend preventing portion 30 connected to the flexible tube portion 8 in a state of covering a proximal end of the flexible tube portion 8, a grasping portion 31 which is linked to the bend preventing portion 30 and which can be grasped by a hand of a user or the like, and an operation portion body 32 linked to a proximal end side of the grasping portion 31. Note that, in the present embodiment, the directions or the like around the insertion axis O in the operation portion 3 are defined based on a state of the user or the like grasping the grasping portion 31, and, more specifically, forward, backward, left and right directions (front, back, left and right side faces, and the like) based on the user or the like grasping the grasping portion 31 are defined for the operation portion 3.

As shown in FIG. 1, the grasping portion 31 is formed in a bilaterally symmetrical shape relative to the insertion axis O (the central axis), and the user or the like can grasp the grasping portion 31 by either a left hand or a right hand similarly.

Further, a treatment instrument insertion portion 35 is provided on a front on a distal end side of the grasping portion 31. The treatment instrument insertion portion 35 is configured having a treatment instrument insertion port 35a through which various kinds of treatment instruments (not shown) are to be inserted. Inside the operation portion 3, the treatment instrument insertion channel 13 is communicated to the treatment instrument insertion port 35a via a branch member not shown. Further, a forceps plug (not shown), which is a cover member for blocking the treatment instrument insertion port 35a, can be detachably attached to the treatment instrument insertion portion 35.

The operation portion body 32 is configured with a hollow member forming a substantially partially spherical shape which is swollen mainly toward left and right sides and forward, on the proximal end side of the grasping portion 31. On a front side of the operation portion body 32, an operation button group 40 for executing various kinds of functions of the endoscope 1 is disposed. On the other hand, a bending lever 45 as an operation lever for performing a bending operation of the bending portion 7 is disposed on a back side of the operation portion body 32. Furthermore, the universal cord 4 is extended from one side portion (for example, a left side portion) of the operation portion body 32.

Here, a left and right shape of the operation portion body 32 is a shape swollen bilaterally symmetrically relative to the insertion axis O. On left and right side faces on a distal end side of the operation portion body 32, guiding recess portions 32a for guiding the forefinger or the like of the user grasping the grasping portion 31 to the operation button group 40 are formed, respectively.

The universal cord 4 extends up to the operation portion 3 from the distal end portion 6 side through the inside of the insertion portion 2, and it is, furthermore, a composite cable in which various kinds of signal lines extending from the operation portion 3, the light guides 12 of a light source apparatus (not shown) and, furthermore, an air/water feeding tube extended from an air/water feeding apparatus (not shown) are inserted inside.

The endoscope connector 5 is configured having an electric connector portion 5a to which a signal cable for connecting to a video processor (not shown), which is an external apparatus, is connected, on a side face portion as well as having a light source connector portion 5b to which the light guides and electric cables connecting to the light source apparatus, which is an external apparatus, are connected, and an air/water feeding plug 5c for connecting an air/water feeding tube (not shown) from the air/water feeding apparatus (not shown), which is an external apparatus.

Next, a configuration of each portion in the operation portion body 32 will be described in more detail.

As shown in FIG. 1, the operation button group 40 is configured having, for example, a suction button 41a as an operation button projecting from a suction valve 41 detachably fitted to the operation portion body 32, and two button switches 42 to which arbitrary functions among the various kinds of functions of the endoscope 1 can be allocated.

The suction button 41a and the button switches 42 are arranged so as to be bilaterally symmetrical on the front side of the operation portion body 32. That is, in the present embodiment, the suction button 41a is disposed at a center in a left and right width direction of the operation portion body 32 so as to be superposed on the insertion axis O. Further, the two button switches 42 are disposed at positions bilaterally symmetrical, with the insertion axis O sandwiched between them, on a more distal end side than the suction button 41a.

Here, for example, as shown in FIG. 4, a cylinder 43 as a button linking member to be linked to the suction valve 41 is provided inside the operation portion body 32. The cylinder 43 is adapted so that the suction valve 41 can be detachably fitted to the cylinder 43, and is disposed at the center in the left and right width direction of the operation portion body 32 so as to be superposed on the insertion axis O to correspond to the disposition of the suction button 41a.

The bending lever 45 is configured with a joystick type lever, for example, tiltable in all directions including the up, down, left and right directions. The bending lever 45 is disposed at a position where the bending lever 45 is bilaterally symmetrical, on the back side of the operation portion body 32. That is, in the present embodiment, the bending lever 45 is disposed at the center in the left and right width direction of the operation portion body 32 so as to be superposed on the insertion axis O. Here, as for the tilt directions of the bending lever 45, for example, the left and right directions of tilt operations are defined as the left and right width direction of the operation portion 3, which is a direction orthogonal to the insertion axis O, and the up and down directions of tilt operations are defined as a direction orthogonal to the left and right width direction, for example, as shown in FIG. 3.

More specifically, the tilt directions of the bending lever 45 of the present embodiment are respectively defined as follows, for example: a left side of FIG. 3 is a tilt direction for causing the bending portion 7 to bend to the left side (a left tilt direction); a right side of FIG. 3 is a tilt direction for causing the bending portion 7 to bend to the right side (a right tilt direction); a lower side of FIG. 3 is a tilt direction for causing the bending portion 7 to bend to an upper side (an up tilt direction); and an upper side of FIG. 3 is a tilt direction for causing the bending portion 7 to bend to a lower side (a down tilt direction).

A finger contact portion 46 which the thumb or the like of the user or the like can be caused to abut is provided at a tip end portion of the bending lever 45. Further, a bending operation mechanism 50 is coupled with a proximal end side of the bending lever 45 inside the operation portion 3, and the bending lever 45 is capable of causing the bending portion 7 to bend in an arbitrary direction via a pulling motion of each pulling wire 23 performed by the bending operation mechanism 50.

As shown in FIGS. 5 to 7, the bending operation mechanism 50 is configured having a housing 51 forming a substantially cylindrical shape, a rotation frame 52 which is pivotally supported so as to be rotatable (swingable) in the housing 51, a base member 53 which is pivotally supported so as to be rotatable (swingable) in the rotation frame 52, and a wire pulling member 54 fixed to the base member 53.

The housing 51 is configured with a member forming a substantially cylindrical shape, and shaft holes 51*a* facing each other are made in a peripheral wall of the housing 51.

The rotation frame 52 is configured with a frame body, for example, forming a substantially rectangular shape. At centers of both longitudinal-direction end portions of the rotation frame 52, a pair of screw holes 52*a* facing each other are made, and, furthermore, at centers of both lateral-direction end portions, a pair of shaft holes 52*b* facing each other are made. By screws 55 inserted in the respective shaft holes 51*a* of the housing 51, respectively, being screwed with the respective screw holes 52*a*, the rotation frame 52 is pivotally supported to be rotatable relative to the housing 51.

The base member 53 is configured with a member forming a substantially cylindrical shape. A fitting hole 53*a* is made at a central part of the base member 53, and the proximal end side of the bending lever 45 is coupled with the fitting hole 53*a* by insertion. Further, a pair of flat portions 53*b* facing each other are formed on a peripheral portion of the base member 53, and screw holes 53*c* facing each other (in FIG. 7, only one of the screw holes 53*c* is shown) are made in the flat portions 53*b*. By screws 56 inserted in the respective shaft holes 52*b* of the rotation frame 52, respectively, being screwed with the respective screw holes 53*c*, the base member 53 is pivotally supported to be rotatable relative to the rotation frame 52. By the base member 53 being supported by the housing 51 via the rotation frame 52 in this way, the bending lever 45 coupled with the base member 53 can tilt in an arbitrary direction.

The wire pulling member 54 is configured with a plate-like member from which arm portions 54*b* are extended in four directions mutually different from one another. More specifically, in the present embodiment, the wire pulling member 54 is configured with a cross-shaped plate-like member in which an angle formed by mutually adjoining arm portions 54*b* is set to be 90 degrees, and central part 54*a* is fixed to the base member 53 via screws 57. That is, the bending lever 45 is coupled with the wire pulling member 54 via the base member 53. Further, on distal end sides of the respective arm portions 54*b*, wire fixing holes 54*c* are made, and proximal end sides of the respective pulling wires 23 extended from an insertion portion 2 side are fixed to the wire fixing holes 54*c*. Thereby, the wire pulling member 54 can pull a predetermined pulling wire 23 corresponding to a tilt state of the bending lever 45 by a predetermined amount of pulling. Note that, the angle formed by the respective arm portions 54*b* is not limited to 90 degrees. For example, the angle can be arbitrarily changed within a range of 90 degrees±30 degrees.

The bending operation mechanism 50 configured as described above is disposed so that the bending operation mechanism 50 faces the cylinder 43 in front and behind in the operation portion body 32. In this case, in the bending operation mechanism 50, the respective arm portions 54*b* are disposed at positions rotated around a central axis OI of the bending lever 45 by an angle within a range of 30 to 60 degrees (for example, positions rotated by 45 degrees) relative to the up, down, left and right tilt directions defined for the bending lever 45. Thereby, for example, as shown in FIG. 4, the bending operation mechanism 50 is arranged in a state that the cylinder 43 is positioned between and faced by two arm portions 54*b* of the wire pulling member 54.

Furthermore, for example, as shown in FIG. 5, two respective stays 58 extending to both sides of the cylinder 43 are provided on the housing 51 of the bending operation mechanism 50; guide coils 23*a* are fixed to the stays 58; and each pulling wire 23 is inserted in the guide coils 23*a* so that the pulling wire 23 is routed, taking a detour to avoid interference with the cylinder 43.

In such a configuration, for example, when the user or the like grasps the grasping portion 31 of the operation portion 3 and causes the bending lever 45 to tilt in the left tilt direction by the thumb of the hand grasping the grasping portion 31, mainly pulling wires 23 coupled with two arm portions 54*b* located in the right tilt direction are pulled. Thereby, mainly two pulling wires 23 located on a left side of a bending direction are pulled in the bending portion 7, and the bending portion 7 is bent to a left side.

Further, for example, when the user or the like grasps the grasping portion 31 of the operation portion 3 and causes the bending lever 45 to tilt in the right tilt direction by the thumb of the hand grasping the grasping portion 31, mainly pulling wires 23 coupled with two arm portions 54*b* located in the left tilt direction are pulled. Thereby, mainly two pulling wires 23 located on a right side of a bending direction are pulled in the bending portion 7, and the bending portion 7 is bent to a right side.

Further, for example, when the user or the like grasps the grasping portion 31 of the operation portion 3 and causes the bending lever 45 to tilt in the up tilt direction by the thumb of the hand grasping the grasping portion 31, mainly pulling wires 23 coupled with two arm portions 54*b* located in the down tilt direction are pulled. Thereby, mainly two pulling wires 23 located on an upper side of a bending direction are pulled in the bending portion 7, and the bending portion 7 is bent to an upper side.

Further, for example, when the user or the like grasps the grasping portion 31 of the operation portion 3 and causes the bending lever 45 to tilt in the down tilt direction by the thumb of the hand grasping the grasping portion 31, mainly pulling wires 23 coupled with two arm portions 54*b* located in the up tilt direction are pulled. Thereby, mainly two pulling wires 23 located on a lower side of a bending direction are pulled in the bending portion 7, and the bending portion 7 is bent to a lower side.

Furthermore, by the user or the like guiding the forefinger or the like of the hand grasping the operation portion 3 along the guiding recess portions 32*a* to the operation button group 40 and performing a pressing operation of the suction button 41*a* and the like while grasping the operation portion 3, the various kinds of functions by the endoscope 1, such as a suction motion, are executed.

At that time, by the operation portion 3 (the grasping portion 31) forming a bilaterally symmetrical shape, and the suction button 41*a* and the bending lever 45 being arranged facing each other at the center in the left and right width direction of the operation portion 3 (the operation portion body 32), it is possible to grasp the operation portion 3 similarly by either the left or right hand, and, moreover, it is possible to manually operate the suction button 41*a* and the bending lever 45 with equal operability. In this case, since the respective arm portions 54*b* are disposed in a state of being rotated around the central axis OI of the bending lever 45 by a predetermined angle relative to the up, down, left and right tilt directions defined for the bending lever 45, it is possible to prevent the arm portions 54*b* and the like from interfering with the cylinder 43. Especially, even when the bending lever 45 is caused to be tilted in the up or down tilt direction, it is possible to prevent the arm portions 54*b*, the pulling wires 23 and the like which are linked with the tilt from interfering with the cylinder 43. Therefore, it is possible to arrange the suction button 41*a* and the bending lever 45 facing each other in front and behind at the center in the left and right width direction of the operation portion 3, without causing the wire pulling member 54 (the bending operation mechanism 50) to be considerably separated from the cylinder 43, and it is possible to realize equal operability by either a left or right hand without upsizing the operation portion 3.

Further, even when the tilt directions of the bending lever 45 are caused to be different from the extending directions of the respective arm portions 54b, around the central axis OI of the bending lever 45 on the operation portion 3 side, it is possible to, by routing the pulling wires 23 to be routed in the bending portion 7 at positions rotated around the insertion axis O by a set angle relative to the up, down, left and right bending directions of the bending portion 7 substantially according to the above state, easily cause the up, down, left and right bending directions of the bending portion 7 to correspond to the up, down, left and right tilt directions defined for the bending lever 45. Furthermore, since it is not necessary to route the pulling wires 23 in the left and right directions in the bending portion 7 if the above disposition is adopted, it is possible to, for example, by using a layout in a bending portion capable of bending only in the up and down directions, in which the image pickup unit 11 which is a large-sized member and the treatment instrument insertion channel 13 are arranged side by side on right and left as it is, realize bending motions in the up, down, left and right directions without increasing an outer diameter.

Note that the present invention is not limited to each embodiment described above, and various modifications and changes are possible. The modifications and changes are also within the technical scope of the present invention. For example, though description has been made on an example in which the present invention is applied to a bronchial endoscope in the embodiment described above, the present invention is not limited to that and is also applicable, for example, to a urinary endoscope or the like.

Further, it goes without saying that the tilt directions defined for the bending lever are not limited to those described above and that the operation buttons are not limited to the suction button and the like.

What is claimed is:

1. An endoscope comprising:
   an insertion portion insertable into a subject and comprising a bending portion bendable in all directions including four directions of up, down, left and right directions with a longitudinal axis as a center;
   four wires configured to cause the bending portion to bend by pulling distal end sides of the four wires being inserted through the insertion portion;
   an operation portion linked to a proximal end of the insertion portion;
   an operation button projectingly disposed at a center in a left and right width direction of the operation portion;
   a button linking member provided in the operation portion and linked to the operation button;
   an operation lever disposed at the center in the left and right width direction of the operation portion so that the operation lever and the operation button face each other as viewed from a front and back of the operation portion, and tiltable in all directions including four directions corresponding to the up, down, left and right directions of the bending portion; and
   a wire pulling member tiltably provided in the operation portion, the operation lever being coupled with a central part of the wire pulling member, and proximal end sides of each of the four wires being coupled with respective distal end sides of four arm portions extended in cross directions from the central part; wherein
   tilt directions of the operation lever for causing the bending portion to bend in the up, down, left and right directions are set to correspond to four directions of the left and right width directions of the operation portion and directions orthogonal to the left and right width directions, respectively;
   extending directions of the four arm portions of the wire pulling member are disposed at positions rotated around a central axis of the operation lever by a set angle within a range of 30 to 60 degrees relative to the four tilt directions set for the operation lever; and
   the button linking member is provided at a position facing the wire pulling member in the center of the right and left width direction of the operation portion and is positioned at an angle relative to the wire pulling member so as to lie between and is faced by two adjacent arm portions among the four arm portions, an angle between the two adjacent arm portions being within a range of 60 to 120 degrees, so that the four arm portions do not interfere with the button linking member.

2. An endoscope comprising: an insertion portion insertable into a subject and comprising a bending portion bendable in all directions including four directions of up, down, left and right directions with a longitudinal axis as a center; four wires configured to cause the bending portion to bend by pulling, distal end sides of the four wires being inserted through the insertion portion; an operation portion linked to a proximal end of the insertion portion; an operation button projectingly disposed at a center in a left and right width direction of the operation portion; a button linking member provided in the operation portion and linked to the operation button; an operation lever disposed at the center in the left and right width direction of the operation portion so that the operation lever and the operation button face each other as viewed from a front and back of the operation portion, and tiltable in all directions including four directions corresponding to the up, down, left and right directions of the bending portion; and a wire pulling member tiltably provided in the operation portion, the operation lever being coupled with a central part of the wire pulling member, and proximal end sides of each of the four wires being coupled with respective distal end sides of four arm portions extended in cross directions from the central part; wherein tilt directions of the operation lever for causing the bending portion to bend in the up, down, left and right directions are set to correspond to four directions of the left and right width directions of the operation portion and directions orthogonal to the left and right width directions, respectively; extending directions of the four arm portions of the wire pulling member are disposed at positions rotated around a central axis of the operation lever by a predetermined angle relative to the four tilt directions set for the operation lever; and the button linking member is provided at a position facing the wire pulling member in the center of the right and left width direction of the operation portion and is positioned at an angle relative to the wire pulling member so as to lie between and is faced by two adjacent arm portions among the four arm portions, an angle between the two adjacent arm portions being within a range of 60 to 120 degrees, so that the four arm portions do not interfere with the button linking member, wherein the four wires are routed at positions rotated around an insertion axis of the insertion portion by a set angle relative to the up, down, left and right directions of the bending portion.

3. The endoscope according to claim 2, wherein the angle by which the four wires are rotated around the insertion axis of the insertion portion is within a range of 30 to 60 degrees relative to the up, down, left and right directions of the bending portion.

4. An endoscope comprising: an insertion portion insertable into a subject and comprising a bending portion bendable in up, down, left and right directions with a longitudinal axis as a center, four wires configured to cause the bending portion to bend by pulling, distal end sides of the four wires being inserted through the insertion portion; an operation portion linked to a proximal end of the insertion portion; an operation button projectingly disposed at a center in a left and right width direction of the operation portion; an operation lever disposed at the center in the left and right width direction of the operation portion so that the operation lever and the operation button face each other as viewed from a front and back of the operation portion, and tiltable in all directions including four directions corresponding to the up, down, left and right directions of the bending portion, wherein tilt directions of the operation lever for causing the bending portion to bend in the up, down, left and right directions are set to correspond to four directions of the left and right width directions of the operation portion and directions orthogonal to the left and right width directions, respectively; a wire pulling member tiltably provided in the operation portion, the operation lever being coupled with a central part of the wire pulling member, and proximal end sides of each of the four wires being coupled with respective distal end sides of four arm portions extended in cross directions from the central part, wherein extending directions of the four arm portions are disposed at positions rotated around a central axis of the operation lever by a first set angle relative to the four tilt directions set for the operation lever; a button linking member provided in the operation portion and linked to the operation button, wherein the button linking member is provided at a position facing the wire pulling member and is positioned at an angle relative to the wire pulling member so as to lie between and is faced by two adjacent arm portions among the four arm portions, an angle between the two adjacent arm portions being within a range of 60 to 120 degrees, so that the four arm portions do not interfere with the button linking member; and wire guides through which the four wires are respectively inserted, the wire guides being provided in the bending portion at positions rotated around an insertion axis of the insertion portion by a second set angle relative to the up, down, left and right directions of the bending portion.

5. The endoscope according to claim 4, wherein the operation lever is tilted in one direction of the four directions set for the operation lever, to thereby cause adjacent two wires among the four wires to be pulled, and cause the bending portion to bend in any one of the up, down, left and right directions.

6. The endoscope according to claim 4, wherein the first set angle and the second set angle are each within a range of 30 degrees to 60 degrees.

* * * * *